United States Patent
Von Arx et al.

(10) Patent No.: US 7,048,542 B2
(45) Date of Patent: May 23, 2006

(54) DENTAL SPLINT

(75) Inventors: Thomas Von Arx, Innerberg (CH); Andreas Filippi, Basel (CH); Joachim Pfefferle, Münstertal (DE)

(73) Assignee: Medartis AG, Basel (CH)

( * ) Notice: Subject to any disclaimer, the term of this patent is extended or adjusted under 35 U.S.C. 154(b) by 331 days.

(21) Appl. No.: 10/344,338

(22) PCT Filed: Aug. 16, 2001

(86) PCT No.: PCT/CH01/00502

§ 371 (c)(1),
(2), (4) Date: Feb. 11, 2003

(87) PCT Pub. No.: WO02/13716

PCT Pub. Date: Feb. 21, 2002

(65) Prior Publication Data

US 2003/0180689 A1 Sep. 25, 2003

(30) Foreign Application Priority Data

Aug. 16, 2000 (CH) ..................................... 1586/00

(51) Int. Cl.
*A61C 5/00* (2006.01)
(52) U.S. Cl. ..................................... 433/215
(58) Field of Classification Search ................ 433/215, 433/18, 9, 19; 606/69, 70
See application file for complete search history.

(56) References Cited

U.S. PATENT DOCUMENTS

| | | | |
|---|---|---|---|
| 3,710,789 A * | 1/1973 | Ersek | ........................... 606/60 |
| 4,433,960 A | 2/1984 | Garito et al. | |
| 4,905,679 A | 3/1990 | Morgan | |
| 4,923,471 A * | 5/1990 | Morgan | ........................ 606/60 |
| 5,087,202 A | 2/1992 | Krenkel | |
| 5,184,955 A | 2/1993 | Baer et al. | |
| 5,609,637 A * | 3/1997 | Biedermann et al. | .... 623/17.16 |
| 5,690,631 A | 11/1997 | Duncan et al. | |
| 5,829,979 A | 11/1998 | Kobashigawa et al. | |
| 6,095,809 A | 8/2000 | Kelly et al. | |

FOREIGN PATENT DOCUMENTS

EP 0 433 852 A1 6/1991

OTHER PUBLICATIONS

International Search Report for International Application No. PCT/CH01/00502.
(No Translation) Product information sheets by Mondeal Medical Systems, GmbH, "Die 3D Titan Ringklebeschiene" (by Christian Krenkel, M.D., D.M.D). The product information sheets include drawings showing a dental splint, which dental splint is shown and described in U.S. Patent No. 5,087,202, U.S. Appl. No. 07/626,296, which serial number is explicitly mentioned in the product information sheets. This type of dental sprint is also discussed in the subject patent application.

(Continued)

*Primary Examiner*—Melba N. Bumgarner
(74) *Attorney, Agent, or Firm*—Welsh & Katz, Ltd.

(57) ABSTRACT

A dental splint for fixing a tooth with increased mobility, which dental splint has several eyes, adjacent eyes being interconnected via a flat connection, and the individual eyes each having a through-opening which is surrounded by a link so that it is possible, by way of the through-opening, to apply an adhesive to the tooth located behind the respective through-opening to secure the dental splint on the tooth, wherein the through-opening of the eye is substantially diamond-shaped, and wherein the flat connection between the eyes is at least approximately twice as wide as the link which surrounds the through-openings.

29 Claims, 2 Drawing Sheets

Figure 3:
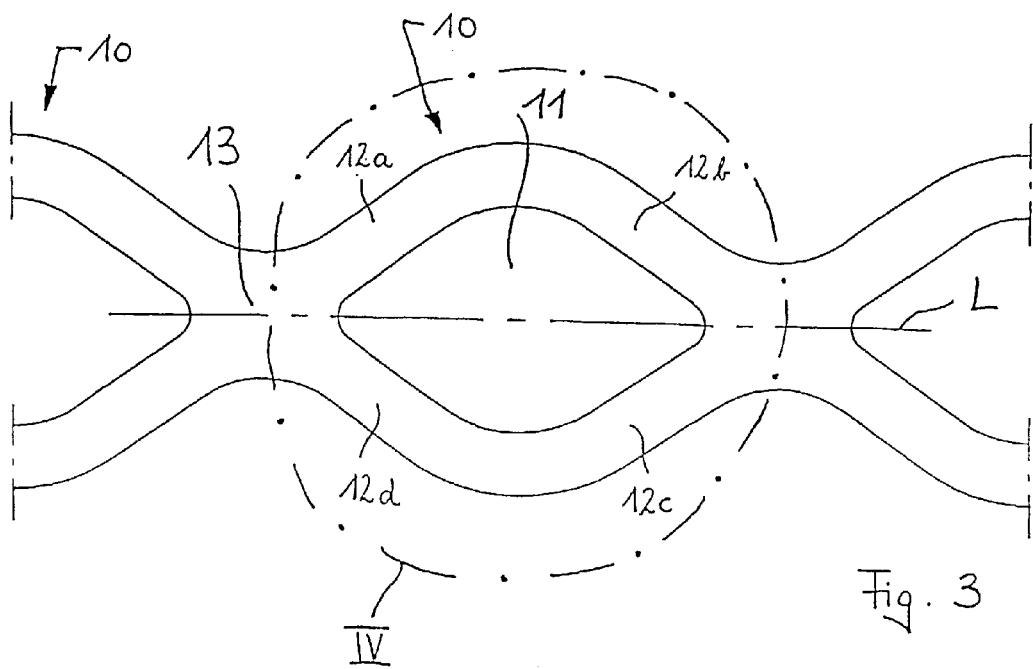

OTHER PUBLICATIONS (No Translation) An article entitled "Reimplantation nach Trauma: Einfluss der Schienung auf die Zahnbeweglichkeit," published by A.. Filippi in "Zachnärzliche Implantologie 16 (2000)". This reference is also mentioned and discussed in the subject patent application.

* cited by examiner

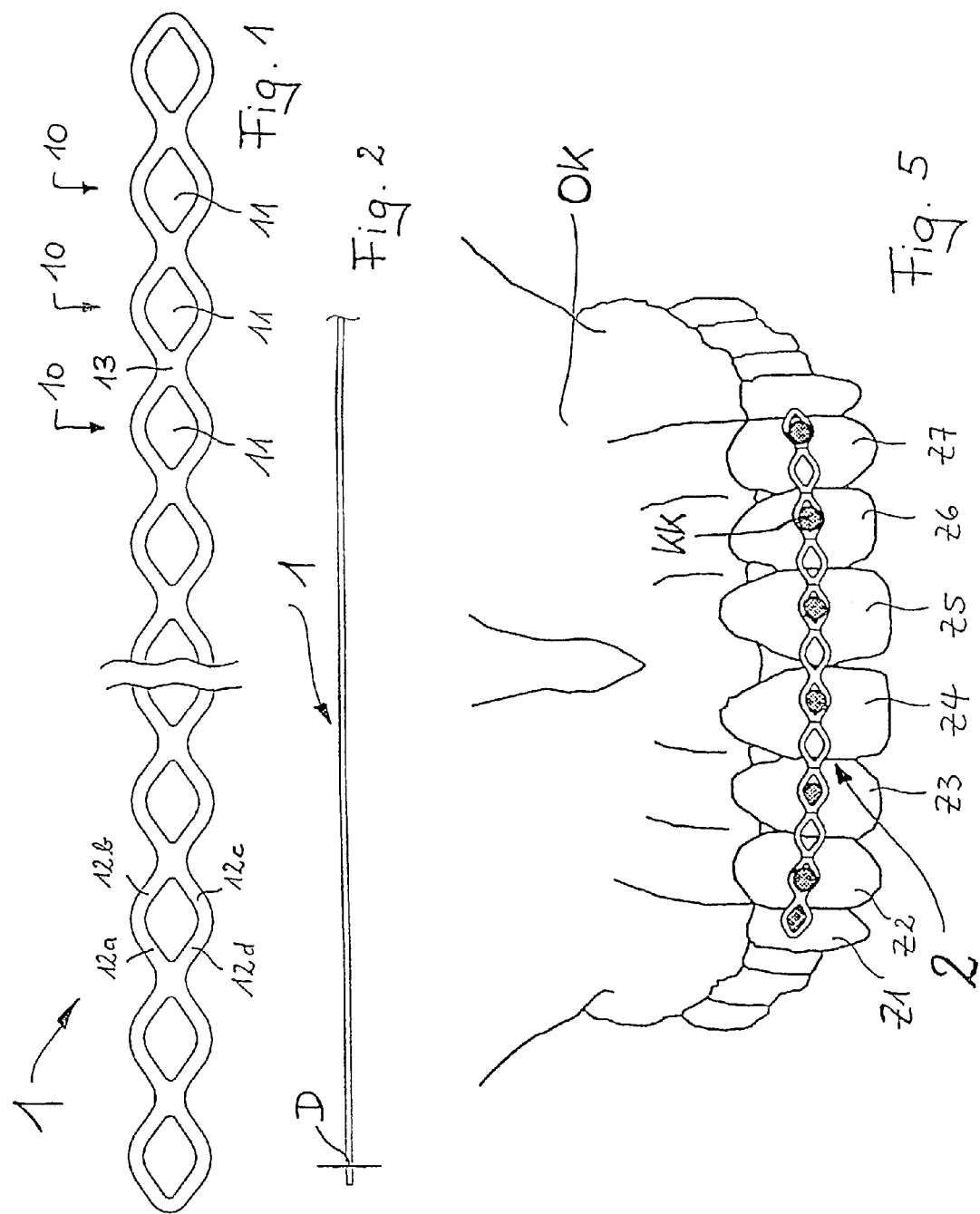

DENTAL SPLINT

The invention relates to a dental splint for fixing a tooth (or a plurality of teeth) with increased mobility in accordance with the preamble of the independent patent claim. The invention further relates to a strip of a material which can be used for dental splints and which has a length which is a multiple of the length of a dental splint.

Dental splints are used, for example, for fixing a traumatized tooth or a plurality of traumatized teeth or for reimplantation of a tooth or of a plurality of teeth. The traumatized (or reimplanted) tooth or the traumatized (or reimplanted) teeth generally have a greatly increased mobility. To fix the traumatized tooth in a desired position, the splint is usually secured on supporting teeth on both sides of the traumatized (or reimplanted) tooth, or of the traumatized (or reimplanted) teeth, and also on the traumatized (or reimplanted) tooth itself or traumatized teeth themselves. Nowadays, the splint is typically secured to the teeth with the aid of an adhesive.

Four types of splints which are all used in practice will be briefly explained below. In this connection, reference is made in particular to the article "Reimplantation nach Trauma: Einfluss der Schienung auf die Zahnbeweglichkeit" [Reimplantation after trauma: Effect of splinting on tooth mobility] by Filippi in "Zahnärztliche Implantologie, No. 16 (2000)", published by Carl Henser Verlag, Munich.

The first type is what is called a "plastic splint". The plastic splint is in principle nothing more than a string of plastic material which extends across the traumatized teeth, and also across the supporting teeth adjoining these on each side, and is bonded to the enamel of the vestibular tooth surfaces by means of an acid-etching technique.

The second type of dental splint is what is called a "wire arch splint". This is in principle nothing more than a section of stable, but plastically deformable and more or less one-dimensional (ie. thin but still stable) wire which, via suitably prepared adhesion surfaces, is bonded, by means of the abovementioned acid-etching technique, to the enamel of the vestibular tooth surfaces, both of the traumatized teeth and also of the supporting teeth adjoining these on each side.

The third type of dental splint is what is called a "bracket splint". This is a dental splint in which flat plates are bonded, by means of the acid-etching technique, to the enamel of the vestibular tooth surfaces, both of the traumatized teeth and of the supporting teeth adjoining these on both sides. These plates have small stubs which project in the labial direction, that is to say in the direction of the lip, and about which a ligature wire is coiled and in this way interconnects the individual plates. If appropriate, the ligature wire can also be twisted between the teeth.

Finally, the fourth type of dental splint is what is called a "ring adhesion splint". The ring adhesion splint in principle has a plurality of annular eyes, the individual eyes arranged adjacent to one another being connected by means of a more or less one-dimensional (ie. thin but still stable) link. Each eye has a through-opening which is surrounded by a link.

The ring adhesion splint is likewise applied using the acid-etching technique. The tooth or teeth with the increased mobility is/are first returned to the desired position, if appropriate under local anesthesia. Application of the splint can then take place, for example by means of the smooth vestibular tooth surfaces being cleaned and then chemically roughened in a certain area by targeted application of an etching fluid. A drop of thin liquid adhesive is then applied to this chemically roughened area. The ring adhesion splint, which has been shaped beforehand, is then placed on the dental arch and pressed into the soft adhesive. Thicker liquid adhesive is then applied via the through-openings of the eyes of the ring adhesion splint in order to connect the links of the eyes, and thus the entire splint, to the vestibular tooth surfaces. In doing so, care must be taken to ensure that the repositioned teeth are kept in the desired position for the duration of hardening of the adhesive (typically only a few seconds).

All these types of dental splints have proven satisfactory in practice, but they have certain aspects which can still be improved. For example, the adhesion surfaces are relatively large, in some splints the level of patient comfort is not optimum, and the splint causes discomfort as a result of too intensive contact with the soft tissue parts, in particular the lips, after application. In other splints, the handling involved when applying the splint is rather awkward. In the case of the wire arch splint, and also the bracket splint, the rotational stability of the splint, that is to say the stability of the splint under torsional loading, could be further improved.

It is therefore an object of the invention to propose a dental splint which is improved in terms of the aforementioned disadvantages.

This object is achieved by the dental splint according to the invention, as characterized by the features of the independent patent claim. Further advantageous embodiments of the dental splint according to the invention are set out in the dependent patent claims. The object is also achieved by a strip of a material which is suitable for dental splints and which in principle can be kept in store as a fairly long storage strip and can, if necessary, then be cut to size to give the length required for the respective dental splint. Advantageous embodiments of this strip, which correspond to those of the splint, are set out in the corresponding dependent patent claims.

The dental splint according to the invention has several eyes, adjacent eyes being interconnected. The individual eyes each have a through-opening which is surrounded by a link, so that it is possible, by way of the through-opening, to apply for example an adhesive to the tooth located behind the respective through-opening in order to secure the dental splint on the tooth. The connection of adjacent eyes is designed as a flat connection, which affords good rotational stability of the splint. In addition, the splint according to the invention can be easily adapted intraorally to the shape of the dental arch or to the contour of the vestibular tooth surfaces. The splint is also easy to remove again, and it also satisfies all the requirements of modern splinting techniques following tooth trauma.

These requirements in particular concern maintaining the physiological tooth mobility, both of the splinted teeth and also of the supporting teeth (the splinted tooth or splinted teeth and the supporting teeth are not completely immobilized by the application of the splint). Rehabilitation is thus rapid and functional. Moreover, excellent hygiene in the area of the splint is ensured, both between the teeth and in the sulcus area). Finally, the splint is easy to adapt on an individual basis.

In one illustrative embodiment of the dental splint according to the invention, the through-opening of the eye is substantially diamond-shaped, and the flat connection between the eyes is at least approximately twice as wide as the link which surrounds the through-openings. This illustrative embodiment of the dental splint is characterized by good rotational stability on the one hand, while, on the other hand, the splint has a certain yield in the direction of the longitudinal axis of the splint and also in a direction transverse to the longitudinal axis of the splint.

In a further illustrative embodiment of the dental splint according to the invention, the splint has a thickness which is in the range of 0.05 mm to 0.5 mm, preferably in the range of 0.1 mm to 0.3 mm, and in particular has a thickness of approximately 0.2 mm. Splints with these dimensions thus have a small thickness, which fact increases patient comfort, but they at the same time ensure the required stability of the splint.

In a further illustrative embodiment of the dental splint according to the invention, the maximum width of the dental splint is in the range of 1 mm to 5 mm, preferably in the range of 2 mm to 3.5 mm, and is in particular approximately 2.8 mm. In this way, more or less the entire patient spectrum can be treated. In principle, a splint with a single width from said range, for example said width of 2.8 mm, is sufficient to cover the entire spectrum of patients (children and adults), because the tooth length (tooth crowns) of the permanent teeth does not vary very much in children and adults. If milk teeth of children are to be splinted, it may in some circumstances be advisable to use a narrower splint because the tooth length (tooth crowns) of milk teeth is shorter than the tooth length (tooth crowns) in permanent teeth.

The dental splint according to the invention is preferably made of a memory-free, plastically deformable, biocompatible material, in particular of titanium, which has particularly good properties in these respects.

The dental splint according to the invention can be single-colored or multi-colored, the word colored being intended to signify a color different than the color of titanium. For children who have to wear such a splint following a trauma, this color may act as an incentive making it easier for them to wear such a dental splint, but it can also quite easily be seen as a fashion statement. Color can be applied for example by anodization.

As has already been mentioned, the object is likewise achieved by means of a strip of a material which can be used for dental splints. Such a strip according to the invention has a length which is a multiple of the length of a dental splint. Like the splint too, the strip has several eyes, adjacent eyes being interconnected. The individual eyes each have a through-opening which is surrounded by a link so that it is possible, by way of the through-opening, to apply an adhesive to the tooth located behind the respective through-opening, in order to secure the dental splint on the tooth. The connection of adjacent eyes is designed as a flat connection, which affords a good rotational stability. Since the strip according to the invention has a length which is a multiple of the length of a dental splint (meaning more than one time the length of the dental splint), the strip according to the invention can easily be cut to the required length depending on the situation presented by the particular patient. The other advantages correspond to the advantages which have already been described above with reference to the dental splint.

In one illustrative embodiment of the strip according to the invention, the through-opening of the eye is substantially diamond-shaped, and the flat connection between the eyes is at least twice as wide as the link which surrounds the through-openings. The corresponding advantages of this illustrative embodiment have already been set out above in the discussion relating to the corresponding illustrative embodiment of the dental splint.

In a further illustrative embodiment of the strip according to the invention, it has a thickness which is in the range of 0.05 mm to 0.5 mm, preferably in the range of 0.1 mm to 0.3 mm, and in particular has a thickness of approximately 0.2 mm. The corresponding advantages of this illustrative embodiment have already been set out above in the discussion relating to the corresponding illustrative embodiment of the dental splint.

In a further illustrative embodiment of the strip according to the invention, the maximum width of the strip is in the range of 1 mm to 5 mm, preferably in the range of 2 mm to 3.5 mm, and is in particular approximately 2.8 mm. The corresponding advantages of this illustrative embodiment have already been set out above in the discussion relating to the corresponding illustrative embodiment of the dental splint.

Finally, according to a further illustrative embodiment of the strip according to the invention, it is made of a memory-free, plastically deformable, biocompatible material, in particular of titanium. The corresponding advantages of this illustrative embodiment have already been set out above in the discussion relating to the corresponding illustrative embodiment of the dental splint.

According to a further illustrative embodiment of the strip according to the invention, it is single-colored or multi-colored, the word colored being intended to signify a color different than the color of titanium. For children who have to wear such a splint following a trauma, this color can act as an incentive making it easier for them to wear such a dental splint, but it can also quite easily be seen as a fashion statement. Color can be applied by anodization for example.

Figure 4:
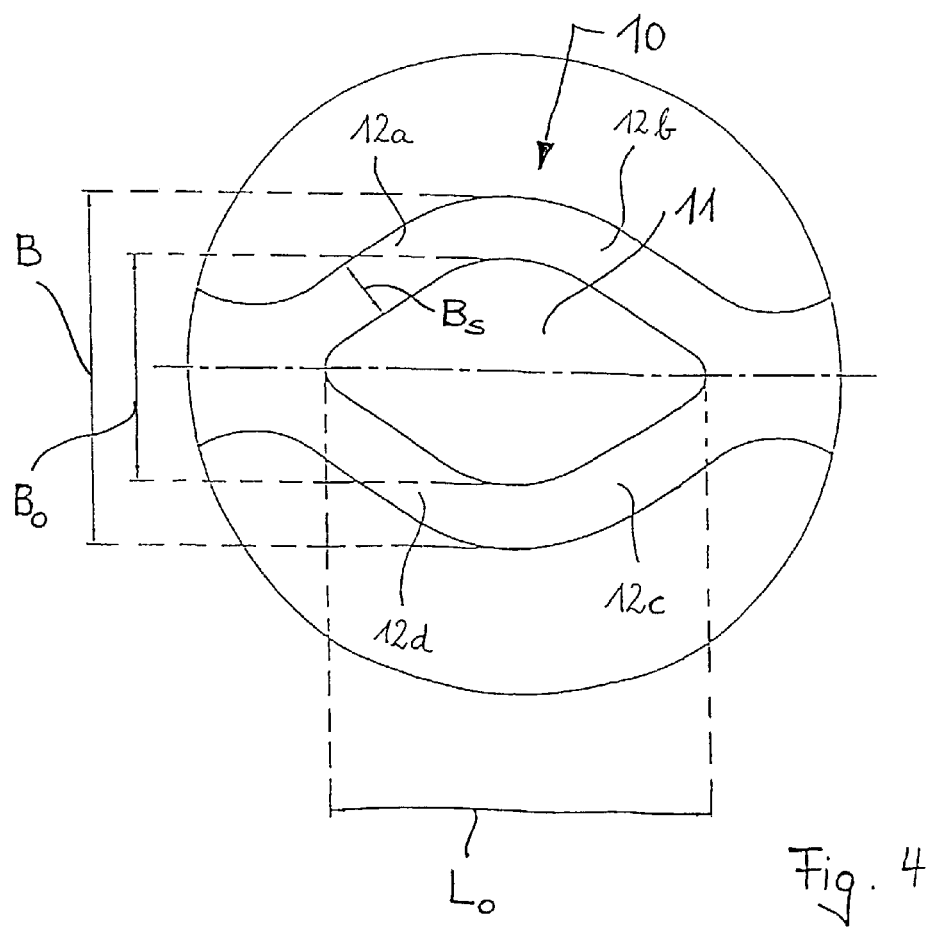

Further advantageous configurations will become evident from the following explanations of illustrative embodiments of the invention, which is explained below with reference to the drawing and its diagrammatic figures, where:

FIG. 1 shows an illustrative embodiment of a strip of a material according to the invention which can be used for dental splints (e.g. titanium), in an enlarged view, FIG. 2 shows, in a side view, part of the strip according to the illustrative embodiment in FIG. 1, illustrating the thickness of the strip, FIG. 3 shows a cutout from FIG. 1 illustrating in particular the flat connection between adjacent eyes, in a further enlarged view, FIG. 4 shows the detail IV from FIG. 3, and FIG. 5 shows an illustrative embodiment of a dental splint according to the invention in situ, the dental splint having been made by cutting the strip from FIG. 1 to the required length.

FIG. 1 depicts an illustrative embodiment of a strip 1 of a material which can be used for dental splints 2, for example the aforementioned titanium. The strip 1 has several eyes 10, each with a through-opening 11. The through-openings 11 are each surrounded by a link which is composed of link parts 12a, 12b, 12c, 12d. Adjacent eyes 10 are interconnected by a flat connection 13, which fact increases the rotational stability of the strip 1.

A dental splint 2—see FIG. 5—can be formed from the strip 1 shown in FIG. 1 by means of a section of desired length being detached from the strip 1 so as to individually fit the respective patient, and the length of the splint 2 can likewise be determined individually for the respective patient and only then is a section of corresponding length detached from the strip 1 kept as storage strip. The length of the strip 1 is in fact a multiple of the length of a dental splint 2.

In the illustrative embodiment according to FIG. 1, the through-openings 11 of the eyes 10 are substantially diamond-shaped, in other words have the shape of a diamond, the individual corners of the diamond being preferably rounded, as is shown here, so that the adjacent link parts 12a, 12b, 12c, 12d merge into one another in a rounded manner.

This configuration of the through-openings 11 can be seen in FIG. 3 and FIG. 4 better than in FIG. 1. The connection 13 of adjacent eyes 10 is designed flat and is at least approximately twice as wide as the link or the individual link parts 12a, 12b, 12c, 12d. A dental splint 2 obtained from such a strip 1 is on the one hand stable in terms of rotation, but on the other hand has a certain (albeit slight) yield both in the direction of the longitudinal axis L of the splint and also in a direction transverse (also including perpendicular) to the longitudinal axis L of the splint.

As can be seen in FIG. 2, the strip 1 and accordingly also the splint 2 has a small thickness D which, in the illustrative embodiment shown, is approximately 0.2 mm, but is generally in the range of 0.05 mm to 0.5 mm, preferably in the range of 0.1 mm to approximately 0.3 mm. The thickness D can depend on the particular material used, and in the illustrative embodiment shown this material is, as has already been explained, the biocompatible material titanium.

In FIG. 4, in which the detail IV from FIG. 3 is shown, the dimensions of an eye 10 in a practical illustrative embodiment of a strip 1 or dental splint 2 are indicated. The width B of the strip 1 or of the dental splint 2 is here approximately 2.8 mm, the width $B_O$ of the through-opening 11 is by contrast approximately 1.8 mm. The width $B_S$ of the link parts 12a, 12b, 12c, 12d can be approximately 0.5 mm. Finally, the length $L_O$ of the through-opening 11 can be approximately 2.8 mm.

In general, the maximum width B of the strip 1 or of the dental splint 2 is in the range of 1 mm to 5 mm, preferably in the range of 2 mm to 3.5 mm, and it is advantageous to keep strips 1 of different width in store in order to be able to select the width B of the dental splint 2 individually for the particular patient and for the particular anatomical situation.

The small dimensions of the strip 1 or of the dental splint 2, in particular the small thickness D, result in good patient comfort. The dental splint 2 can in practice hardly be felt, or only very slightly, since only comparatively small adhesion surfaces (and correspondingly less adhesive) are needed, and good hygiene is ensured both between the teeth and in the area of the sulcus. At the same time, however, the dental splint satisfies the requirements of modern splinting techniques following tooth trauma in respect of maintaining the physiological mobility of the traumatized teeth and also of the supporting teeth. It guarantees rapid and functional rehabilitation, and this with individual adaptability of the dental splint 2.

As has already been stated, the described illustrative embodiment of the strip 1 according to the invention or of the dental splint 2 according to the invention is made of titanium. In general, however, the strip 1 or dental splint 2 can be made of a memory-free, plastically deformable, biocompatible material.

The strip 1 or dental splint 2 preferably made of titanium can be single-colored or multi-colored, the word colored in this context signifying a color different than the color of titanium. For children who have to wear such a splint following a trauma, this color can act as an incentive making it easier for them to wear such a dental splint, but it can also quite easily be seen as a fashion statement when such a dental splint has to be worn.

The described illustrative embodiment of the titanium strip 1 according to the invention can be produced by both the outer contour of the strip 1 and also the through-openings 11 being formed by laser cutting. Alternatively, other methods such as punching, stretching, an etching technique or water-jet cutting may be also considered.

Finally, FIG. 5 shows a dental splint 2 in situ, having been cut to the optimum length from a strip 1 of the desired width B. An upper jaw OK is shown in which the dental splint 2 extends across the teeth Z1, Z2, Z3, Z4, Z5, Z6, Z7. For example, the teeth Z4 and Z5 can be the teeth with the increased mobility, so that the remaining teeth Z1, Z2, Z3, Z6, Z7 function as supporting teeth.

The dental splint 2 is applied by means of the already described acid-etching technique, that is to say the splint is therefore bonded to the cleaned and (chemically) roughened teeth by means of a plastic adhesive KK. The small dimensions of the dental splint 2 in relation to the teeth Z1–Z7 can be clearly seen in FIG. 5 and once again underlines the high level of patient comfort. For the physician carrying out the treatment, the dental splint 2 is easy and comfortable to maneuver, so that the dental splint 2 is also convenient from the point of view of handling.

The invention claimed is:

1. A method for fixing a traumatized or re-implanted tooth or for fixing a plurality of traumatized or re-implanted teeth having an increased mobility, comprising:
    providing a dental splint having several eyes, with adjacent eyes being interconnected via a flat connection, and each eye having a through-opening which is surrounded by a link;
    positioning the dental splint in front of the tooth or teeth such that the dental splint extends over the traumatized or reimplanted tooth or teeth; and
    applying an adhesive by way of the through-opening to the tooth located behind the respective through-opening to secure the dental splint on the tooth, wherein the through-opening of the eye is substantially diamond-shaped, and wherein the flat connection between the eyes is at least approximately twice as wide as the link which surrounds the through-openings.

2. The method according to claim 1, wherein the splint has a thickness which is in the range of 0.05 mm to 0.5 mm.

3. The method according to claim 1, wherein the maximum width of the dental splint is in the range of 1 mm to 5 mm.

4. The method according to claim 1, wherein the dental splint is made of a memory-free, plastically deformable, biocompatible material.

5. The method according to claim 4, wherein the dental splint is made of titanium.

6. The method according to claim 1, wherein the dental splint is single-colored or multi-colored.

7. The method according to claim 1, wherein the splint has a thickness which is in the range of 0.1 mm to 0.3 mm.

8. The method according to claim 1, wherein the splint has a thickness of approximately 0.2 mm.

9. The method according to claim 1, wherein the maximum width of the dental splint is in the range of 2 mm to 3.5 mm.

10. The method according to claim 1, wherein the maximum width of the dental splint is approximately 2.8 mm.

11. A method for fixing a traumatized or re-implanted tooth or for fixing a plurality of traumatized or re-implanted teeth, the method comprising:
    providing a strip of a material having a length which is a multiple of the length of a dental splint, and said strip having several eyes, with adjacent eyes being interconnected via a flat connection, and each eye having a through-opening which is surrounded by a link; and
    cutting the strip of material to form a dental splint;

positioning the dental splint in front of the tooth or teeth such that the splint extends over the traumatized or reimplanted tooth or teeth;

applying an adhesive by way of the through-opening to the tooth located behind the respective through-opening to secure the dental splint on the tooth, wherein the through-opening of the eye is substantially diamond-shaped, and wherein the flat connection between the eyes is at least approximately twice as wide as the link which surrounds the through-openings.

12. The method according to claim 11, wherein the strip has a thickness which is in the range of 0.05 mm to 0.5 mm.

13. The method according to claim 11, wherein a maximum width of the strip is in the range of 1 mm to 5 mm.

14. The method according to claim 11, wherein the strip is made of a memory-free, plastically deformable, biocompatible material.

15. The method according to claim 14, wherein the strip is made of titanium.

16. The method according to claim 11, wherein the strip is single-colored or multi-colored.

17. The method according to claim 11, wherein the strip has a thickness which is in the range of 0.1 mm to 0.3 mm.

18. The method according to claim 11, wherein the strip has a thickness of approximately 0.2 mm.

19. The method according to claim 11, wherein a maximum width of the strip is in the range of 2 mm to 3.5 mm.

20. The method according to claim 11, wherein a maximum width of the strip is approximately 2.8 mm.

21. A method for fixing a traumatized or re-implanted tooth or for fixing a plurality of traumatized or re-implanted teeth having an increased mobility, the method comprising:

providing a dental splint having a thickness of about 0.05 mm to 0.5 mm and a width of about 1 mm to 5 mm, and further having a plurality of eyes, wherein adjacent eyes are interconnected via a flat connection, and each eye includes a through-opening surrounded by a link to facilitate application of an adhesive to a tooth located behind the respective through-opening, wherein the through-opening is substantially diamond-shaped and wherein the flat connection between the eyes is at least approximately twice as wide as the link surrounding the through-openings;

positioning the dental splint on the traumatized or re-implanted tooth or teeth having the increased mobility such that the dental splint extends over the traumatized or reimplanted tooth or teeth as well as over at least one supporting tooth at either side of the tooth or teeth having the increased mobility; and applying an adhesive by way of the through-openings to the respective teeth located behind the through-openings of the dental splint to secure the dental splint on the teeth, so as to fix the traumatized or reimplanted tooth or teeth.

22. A method according to claim 21, wherein the surface of the teeth onto which the dental splint is to be secured is chemically roughened using an acid-etching technique prior to applying the adhesive.

23. The method according to claim 21, wherein the dental splint is made of a memory-free, plastically deformable, biocompatible material.

24. The method according to claim 23, wherein the dental splint is made of titanium.

25. The method according to claim 21, wherein the dental splint is single-colored or multi-colored.

26. The method according to claim 21, wherein the splint has a thickness which is in the range of 0.1 mm to 0.3 mm.

27. The method according to claim 21, wherein the splint has a thickness of approximately 0.2 mm.

28. The method according to claim 21, wherein the maximum width of the dental splint is in the range of 2 mm to 3.5 mm.

29. The method according to claim 21, wherein the maximum width of the dental splint is approximately 2.8 mm.

\* \* \* \* \*